United States Patent [19]

Ohtani et al.

[11] Patent Number: 5,763,647
[45] Date of Patent: Jun. 9, 1998

[54] PREPARATION OF OPTICALLY ACTIVE 1,4-BRIDGED-CYCLOHEXANE CARBOXYLIC ACID DERIVATIVES

[75] Inventors: Mitsuaki Ohtani, Nara; Hisanori Takahashi, Kawanishi; Fumihiko Watanabe, Kitakatsuragi; Masami Takayama, Nara, all of Japan

[73] Assignee: Shionogi & Co., LTD., Osaka, Japan

[21] Appl. No.: 893,456

[22] Filed: Jul. 11, 1997

Related U.S. Application Data

[63] Continuation of Ser. No. 938,458, Sep. 1, 1992, abandoned, which is a continuation-in-part of Ser. No. 673,755, Mar. 25, 1991, abandoned.

[30] Foreign Application Priority Data

Mar. 30, 1990 [JP] Japan ........................ 2-85443

[51] Int. Cl.⁶ .................................................. C07C 209/88
[52] U.S. Cl. .................... 562/402; 562/401; 564/302; 564/303; 564/460
[58] Field of Search ........................... 564/302, 303, 564/460; 562/401, 402

[56] References Cited

U.S. PATENT DOCUMENTS

| | | | |
|---|---|---|---|
| 3,085,110 | 4/1963 | Young | 564/303 |
| 3,553,257 | 1/1971 | Halmos et al. | 564/303 |
| 4,085,138 | 4/1978 | Whitney | 564/303 |
| 4,097,490 | 6/1978 | Reinhold | 564/303 |
| 4,576,959 | 3/1986 | Flaugh | 514/411 |
| 4,861,913 | 8/1989 | Narisada et al. | 549/80 X |

FOREIGN PATENT DOCUMENTS

| | | |
|---|---|---|
| 0 085 023 | 8/1983 | European Pat. Off. ........ 564/303 |
| 0 226 346 | 6/1987 | European Pat. Off. |
| 2 100 823 | 3/1972 | France |

OTHER PUBLICATIONS

Karrer, Organic Chemistry, 4th English Edition, 1950, pp. 103–104.
Narisada et al., J. Med. Chem., 1988, 31, pp. 1847–1854.
Houben–weyl, Methoden Der Organischen Chemie, vol. IV, part 2 (1955) pp. 513–519.
Narisada et al., Patent Abstracts of Japan, vol. 13, no. 107 (C–576) (3455) 14 Mar., 1989 JP-A-69 284 158.
Irwin et al., J.A.C.S. 98;26, dec. 22, 1976, pp. 8476–8481.

*Primary Examiner*—Brian M. Burn
*Attorney, Agent, or Firm*—Wenderoth, Lind & Ponack

[57] ABSTRACT

A process for preparing an optically active 1,4-bridged-cyclohexane carboxylic acid derivatives which are clinically important thromboxane $A_2$ thromboxane of formula (IV):

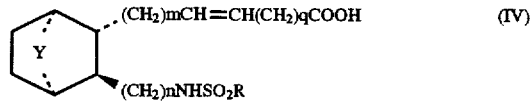

(IV)

wherein, R is phenyl or phenyl substituted with hydroxy, lower alkoxy, halogen, or lower alkyl; Y is oxygen, methylene, substituted methylene; m is 0 or 1; n is 0, 1 or 2; q is 3 or 4 with the proviso that when m is 1, n is 0 or 1 from an optically active norbornyl amine derivative.

4 Claims, No Drawings

PREPARATION OF OPTICALLY ACTIVE 1,4-BRIDGED-CYCLOHEXANE CARBOXYLIC ACID DERIVATIVES

This application is a continuation of now abandoned application Ser. No. 07/938,458, filed Sep. 1, 1992, which application is a continuation-in-part application of now abandoned application Ser. No. 07/673,755, filed Mar. 25, 1991.

FIELD OF THE INVENTION

This invention relates to a method for preparing optically active 1,4-bridged-cyclohexane carboxylic acid derivatives which are clinically important thromboxane $A_2$ ($TXA_2$) receptor antagonists of formula (IV):

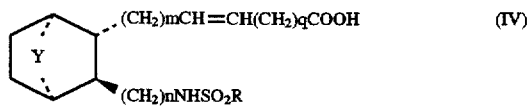

wherein R is phenyl or phenyl substituted with hydroxy, lower alkoxy, halogen, or lower alkyl; Y is oxygen, methylene, substituted methylene; m is 0 or 1; n is 0, 1 or 2; q is 3 or 4 with the proviso that when m is 1, n is 0 or 1.

BACKGROUND OF THE INVENTION $TXA_2$ is a member of the prostanoids which are biologically active substances and synthesized enzymatically from arachidonic acid in various animal tissues. $TXA_2$ has been proved to exhibit many significant biological activities, such as aggregation of platelets and contraction of smooth muscle of various organs. Therefore, $TXA_2$ receptor antagonists have been expected to be therapeutically and prophylactically effective on $TXA_2$-associated diseases. Such diseases include myocardial infarction, pulmonary embolism, thrombosis, encyopyelitis, renal dysfunction, cerebral infarction, asthma caused by bronchoconstriction, arterial sclerosis and the like. It may be also useful to prevent the vascular contraction after a subarchnoidal bleeding. $TXA_2$ shocks after the artery reperfuse of circulation systems or digestive organs, shocks caused by bleeding, septicemia, wound, cardiac dysfunction, endotoxin, acute pancreatitis, burn, or the like. It may be effective for the prevention of thrombocytopenia during extracorporeal circulation.

In view of the above, the present inventors had made extensive study and found a class of 1,4-bridged cyclohexane carboxylic acids having antagonistic activities against $TXA_2$ [Japanese Patent Publication (Kokai) No. 139161/1988, *** U.S. Pat. No. 4,861,913, and Narisada, M. et al, J. Med. Chem. 31, 1847–1854 (1988)]. Further investigations proved that certain optical isomers thereof, which are generally shown by the above formula (IV), are superior to racemic mixtures. Among them, a compound named (+)-S-145 of formula (IV) where R is phenyl, Y is methylene, m is 1, n is 0, and q is 3 proved to be a highly effective and clinically useful $TXA_2$ receptor antagonist.

Therefore, it has been desired to produce preferentially optical isomers of formula (IV) to improve the therapeutic effects on the above-mentioned diseases. Before the present invention, the optically active carboxylic acids (IV) have been mainly obtained by resolving a racemic mixture using conventional methods such as chiral chromatography (HLPC). However, such resolution method was not effective enough to apply to a large scale production of optically active compound of formula (IV) because the carboxyl moiety is too far removed from the chiral center.

Although asymmetric synthesis can be used, it still has problems in yield, cost, and the like.

To overcome these drawbacks, it was suggested to use an optically active intermediate in the early stage of the process for the preparation of the carboxylic acid (IV). For example, the above-mentioned (+)-S-145 can be produced using an optically active sulfonamide which can be prepared from an optically active norcamphor according to the following reaction scheme.

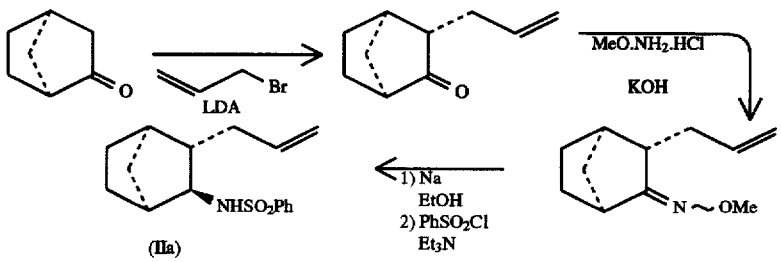

(IIa)

The optically active starting material, norcamphor, can be prepared according to a troublesome procedure described by J. B. Jones (JACS, 98:8476 (1976)) which requires as many as 10 times of recrystallization. Narisada et al applied the Jones' method to the total process for the preparation of compound (IV) (Narisada et al., J. Med. Chem. 31: 1847–1854, 1988) and reported that 20 time recrystallization was needed (ibid, pp. 1847–1854, esp. page 1849). Thus, the poor yield of norcamphor lowers the yield of sulfonamide, resulting in insufficient yield of (+) -S-145.

Accordingly, it has been requested to establish a method for an efficient preparation of an optically active intermediate or starting material, said method being applicable to the industrial preparation of compound (IV).

The inventors have found that a racemic mixture of a norbornyl amine of formula (I):

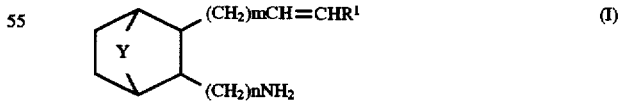

wherein $R^1$ is hydrogen, lower alkyl or lower alkyl substituted with —$COOR^3$ at the terminal methylene residue; $R^3$ is lower alkyl; Y is oxygen, methylene or substituted methylene; m is 0 or 1; n is 0, 1 or 2 with the proviso that when m is 1, n is 0 or 1, when treated with a certain chiral acid, forms diastereomeric salts consisting of diastereoisomers which differ from each other in physicochemical properties such as solubility in a selected solvent, whereby the salt of the desired optical isomer can be separated easily from the other. For purposes of the invention, the compound of formula (I) and intermediates derivated from the compound (I) according to the method of the present invention are hereinafter referred to as norbornyl compounds irrespective of what Y represents because typical compounds of formula (I) wherein Y is methylene are known as "norbornane derivatives", and the terms "diastereomeric salt" and "chiral salt" are herein used exchangeably. The chiral salt, when treated by a conventional method, gives the desired optically active norbornyl amine of formula (I'):

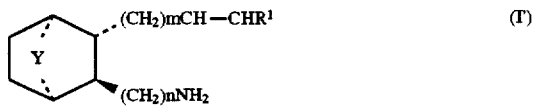

wherein $R^1$, Y, m and n are as defined above.

DESCRIPTION OF THE INVENTION

Thus, the present invention provides a process for preparing a compound of formula (IV):

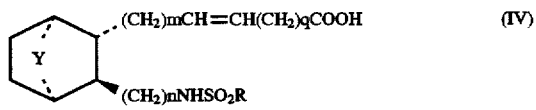

wherein R is phenyl or phenyl substituted with hydroxy, lower alkoxy, halogen, or lower alkyl; Y is oxygen, methylene, substituted methylene; m is 0 or 1; n is 0, 1 or 2; q is 3 or 4 with the proviso that when m is 1, n is 0 or 1, which comprises the following reaction steps:

(a) resolving a compound of formula (I):

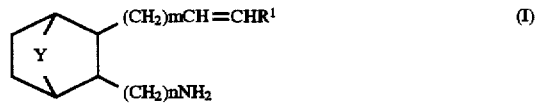

wherein $R^1$ is hydrogen, lower alkyl or lower alkyl substituted with —$COOR^3$ at the terminal methyl residue; $R^3$ is lower alkyl and Y, m and n are as defined above with a chiral acid selected from the group consisting of (−)-D-tartaric acid, (−)-O-diacetyl-L-tartaric acid, (−)-O-dibenzoyl-L-tartaric acid, (−)-D-mandelic acid, N-acetyl-L-leucine, N-acetyl-L-glutamic acid, N-acetyl-L-phenylalanine, and N-tert-butoxycarbonyl-L-methionine in an appropriate solvent to form a chiral salt;

(b) recovering an optically active amine of formula (I'):

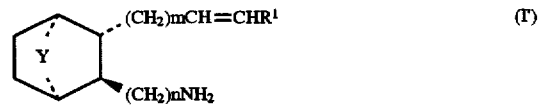

wherein $R^1$, Y, m and n are as defined above by treating the chiral salt obtained in step (a) with a base;

(c) reacting the optically active compound of formula (I') obtained in step (b) with a substituted sulfonyl halide of formula (III):

wherein R is as defined above and X is halogen to yield an optically active sulfonamide derivative of formula (II):

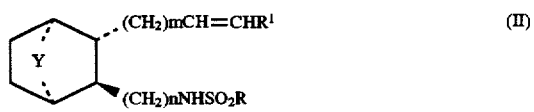

wherein $R^1$, R, Y, m, and n are as defined above;

(d) oxidizing the compound (II) prepared in step (c) to yield an aldehyde of formula (II'):

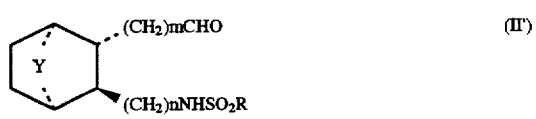

wherein R, Y, m, and n are as defined above; and (e) converting the aldehyde (II') prepared in step (d) into a compound of formula (IV) by a conventional method.

For purposes of the present invention, as disclosed and claimed herein, the following terms are defined below.

The term "lower alkyl" refers to a straight or branched saturated hydrocarbon radical having one to eight carbon atoms, including methyl, ethyl, n-propyl, isopropyl, butyl, isobutyl, sec-butyl, tert-butyl, pentyl, isopentyl, neopentyl, 1-methylbutyl, 1,2-dimethylbutyl, hexyl, heptyl, octyl, and the like.

In the definition of "substituted sulfonyl halide", examples of halogen include chlorine, bromine, and the like and those of substituents include phenyl or phenyl substituted with hydroxy; halogen such as chlorine, bromine, and the like; lower alkyl such as methyl, ethyl, and the like; and lower alkoxy such as methoxy, ethoxy, and the like. Examples of substituted sulfonyl halide are benzenesulfonyl chloride, methoxybenzenesulfonyl chloride, hydroxybenzenesulfonyl chloride, toluenesulfonyl chloride, bromobenzenesulfonyl bromide, and the like.

According to the present invention, the clinically useful thromboxane $A_2$ ($TXA_2$) receptor antagonists, i.e., 1,4-bridged-cyclohexane carboxylic acid derivatives of formula (IV), can be produced in large scale. The each step consisting of the process of the invention can be carried out using any of well known methods though, the industrially useful overall process for the preparation of compound (IV) is disclosed by the present invention for the first time. The individual step will be hereinafter described in detail.

Step (a)

The starting material of step (a), a racemic mixture of norbornyl amine derivative (I), can be prepared according to various procedures well-known in the field of organic chemistry. The procedures can be found in literatures including the Japanese Patent Publication (KOKAI) Nos. 139161/1988 and 284158/1988.

Although the method for resolving a racemic mixture of amine by forming diastereomeric salt with a chiral acid has been known, no reports have been found that a racemic mixture of norbornyl amine of formula (I) having alkyl or alkylene side chains at the 2-position of the cyclohexane ring can be successfully resolved prior to the present invention.

The resolution is accomplished by treating a racemic mixture of compound (I) with a selected chiral acid in an appropriate solvent and allowing the mixture to react at about −20° C. to about 100° C., preferably about 0° C. to 80° C. for about 1 minute to about 60 minutes, preferably about 1 minute to 30 minutes. When the reaction mixture is allowed to stand for at about 0° C. to about 40° C. for about 1 hour to about 24 hours, either isomer of diastereomeric salt precipitates.

Examples of appropriate solvents are organic solvents selected from those in which either isomer of a chiral salt formed can hardly or never dissolve so that a resultant diastereomeric salt can be separated conveniently by, for example, filtration. Preferred solvents are alcoholic solvents including methanol, ethanol, propanol and the like.

The chiral acid, the resolving agent, which can be used in the present invention is selected from optically active acids known as resolving agents to those skilled in the art. Examples of chiral acid usable in the present invention are mono- or di-carboxylic acid, or derivatives thereof such as (−)-D-mandelic acid, (−)-D-tartaric acid, (−)-O-monoacetyl-L-tartaric acid, (−)-O-diacetyl-L-tartaric acid, (−)-O-monobenzoyl-L-tartaric, (−)-O-dibenzoyl-L-tartaric acid, (−)-O-monopivaloyl-L-tartaric, (−)-O-dipivaloyl-L-tartaric acid, and the like; or N-protected amino acids such as L-alanine, L-valine, L-leucine, L-isoleucine, L-serine, L-threonine, L-methionine, L-proline, L-aspartic acid, L-glutamic acid, L-asparagine, L-glutamine, L-histidine, L-lysine, L-arginine, L-phenylalanine, L-tyrosine, L-tryptophan, D-phenylglycine, and the like. Examples of amino-protecting groups are $C_2$–$C_6$ acyl optionally substituted with phenyl; benzoyl; $C_1$–$C_5$ alkoxycarbonyl optionally substituted with phenyl; phenyloxycarbonyl; phenylsulfonyl; lower alkylsulfonyl; carbamoyl, and the like. The phenyl substituent may be also substitued with substituents such as hydroxyl group, halogen atom, lower alkyl, and the like.

Particularly preferred resolving agents are (−)-D-tartaric acid, (−)-O-diacetyl-L-tartaric acid, (−)-O-dibenzoyl-L-tartaric acid, (−)-D-mandelic acid, N-acetyl-L-leucine, N-acetyl-L-glutamic acid, N-acetyl-L-phenylalanine, N-tert-butoxycarbonyl-L-methionine, and the like. The resolving agent is generally used in the ratio of about 0.5 to about 1 mole per 1 mole of compound (I) as a racemic mixture.

Step (b)

The precipitated chiral salt is separated by, for example, filtration and an optically active norbornyl amine is recovered by treating the precipitate conventionally, for example, with a base such as metal hydroxide (e.g., lithium hydroxide, sodium hydroxide, potassium hydroxide), triethyl amine, DBN, or the like to give an optically active norbornyl amine (I'). The amine (I') is then purified by a conventional method, if desired.

Step (c)

In this step, the resultant optically active amine (I') is reacted with a substituted sulfonyl halide of formula (III) in an appropriate solvent under a basic condition at room temperature for about 10 minutes to 1 hour.

Examples of bases which can be used in the reaction include organic amines such as pyridine, triethyl amine and the like, inorganic bases such as sodium hydroxide, potassium hydroxide, sodium carbonate, potassium carbonate, sodium hydrogencarbonate and the like.

Examples of substituted sulfonyl halide include methanesulfonyl chloride, ethanesulfonyl chloride, propanesulfonyl chloride, butanesulfonyl chloride, pentanesulfonyl chloride, hexanesulfonyl chloride, heptanesulfonyl chloride, octanesulfonyl chloride, benzenesulfonyl chloride, methoxybenzenesulfonyl chloride, nitrobenzenesulfonyl chloride, acetoxybenzenesulfonyl chloride, toluenesulfonyl chloride, ethylbenzenesulfonyl chloride, aminobenzenesulfonyl chloride, acetylaminobenzenesulfonyl chloride, dimethylaminobenzenesulfonyl chloride, bromobenzenesulfonyl bromide and the like.

Examples of appropriate solvents include chlorinated hydrocarbons such as chloroform, dichloromethane and the like, ethers such as diethyl ether, tetrahydrofuran and the like, and aromatic solvents such as benzene and the like, or a two-layer solvent system consisting of either of these organic solvents and water.

Alternatively, the chiral salt obtained in step (a) can be conveniently reacted as it is with sulfonyl halide (III) in the presence of a base as described above such as sodium hydroxide, potassium hydroxide or triethylamine in a solvent such as alcoholic solvent, water, ethyl acetate, and the like, or a mixture thereof. By this method, the desired optically active sulfonamide derivative (II) can be obtained in high optical yield.

Both of the above methods for the production of sulfonamide (II) have advantages over the above-mentioned conventional methods which employ an optically active norcamphor as a starting material.

Step (d)

The oxidation of sulfonamide (II) can be conducted using any of known methods to one of skill. For example, the allyl group of compound (II) is oxidized into an epoxide, which is then oxidatively cleaved to give an aldehyde of formula (II'). The oxidization of sulfonamide (II) can be carried out by ozone cleavage, or using conventional oxidizing agents. Examples of oxidizing agents include osmic acid-periodic acid, osmic acid-chromic acid, osmic acid-lead tetraacetate, ruthenium tetroxide-periodic acid, ruthenium tetroxide-chromic acid, ruthenium tetroxide-lead tetraacetate, potassium permanganate-periodic acid, potassium permanganate-chromic acid, potassium permanganate-lead tetraacetate and the like. Although the oxidation of compound (II) is hereinafter described using the method where allyl group is converted into an epoxide, which in turn into aldehyde (II'), the present invention is not limited to this method but includes any known methods which give the desired aldehyde (II').

The oxidation of allyl group to an epoxide can be conducted using oxidizing agents such as a combination of hydrogen peroxide and transition metal as a catalyst, or peracids or peracid esters such as performic acid, peracetic acid, perbenzoic acid, monoperphthalic acid, monopermaleic acid, pertrifluoroacetic acid, m-chloroperbenzoic acid, p-nitroperbenzoic acid, or the like.

Examples of solvent include ether solvents such as ether, tetrahydrofuran and the like, chlorinated hydrocarbons such as dichloromethane, chloroform and the like, or water. The reaction can be conducted at a temperature ranging from 0° C. to room temperature for several minutes to several hours.

As the next step, the epoxide thus formed is converted into the aldehyde (II') through the oxidative cleavage of the glycol formed by hydration.

An oxidizing agent which also serves as hydration catalyst can be selected from those derived from periodic acid including periodic acid, o-periodic acid and the like. Solvents which can be used in this reaction are preferably water-miscible ones such as ether, tetrahydrofuran, dioxane and the like. The reaction can be carried out at room temperature for several tens of minutes to several hours.

Step (e)

In this step, the aldehyde (II') is allowed to react with an ylide to generate a double bond. Alternatively, the formation of a double bond can be conducted through the known Aldol condensation and dehydration. The former method will be hereinafter described in detail, however, it is not intended to restrict the present invention.

The reaction can be carried out in accordance with the conventional Wittig reaction. Ylides, which can be shown by a general formula:

$(R^4)_3P=CH(CH_2)_qCOOM$ wherein $R^4$ is $C_1$–$C_8$ alkyl or aryl, M is an alkali metal and q is as defined above, are readily prepared from phosphine such as triphenylphosphine by the reaction with a halide of desired alkyl to be condensed such as 5-bromopentanoic acid, 3-bromopropanoic acid or the like in the presence of a base. Examples of bases include dimsyl sodium, dimsyl potassium, sodium hydride, n-butyl lithium, potassium t-butoxide, lithium di-isopropylamide and the like. The reaction can be carried out at −30° to 80° C. for several hours in a solvent such as ether, tetrahydrofuran, n-hexane, dimethyl sulfoxide, or t-butyl alcohol.

Although all compounds of formula (I) are suitable for the method of present invention, certain classes of compounds are especially preferred for purposes of the invention.

Preferred norbornyl amines are those compounds of formula (I) wherein $R^1$ is hydrogen or propyl having $COOR^3$ at the terminal thereof; $R^3$ is lower alkyl; Y is methylene or oxygen; and m is 0 or 1 and n is 0 or 1. Particularly preferred norbornyl amine is a compound of formula (I) wherein $R^1$ is hydrogen; Y is methylene; m is 1; and n is 0.

Preferred optically active sulfonamide derivatives of formula (II) are those obtainable from the preferred amines as mentioned above. Specifically, they are shown by formula (II) wherein $R^1$ is hydrogen or propyl having $COOR^3$ at the terminal thereof; $R^2$ is phenyl, p-tolyl, 4-bromophenyl. A compound shown by formula (II) wherein $R^1$ is hydrogen, $R^2$ is phenyl; Y is methylene; and m is 1 and n is 0 is novel and particularly useful as an intermediate for the production of above mentioned (+)-S-145.

The following example is set forth to further describe the invention but is in no way meant to be construed as limiting the scope thereof.

EXAMPLE 1

Optical Resolution of Racemic Mixture of Norbornyl Amine using (−)-D-Tartaric Acid To a solution of 4.50 g (30 mM) of (−)-D-tartaric acid in 100 ml of ethanol is added a solution of 4.54 g (30 mM) of racemic mixture of amine (Ia) in 40 ml of ethanol at 70°–80° C. over 2 minutes and allowed to cool to room temperature. When the mixture is stirred at room temperature, the product begins to precipitate. After stirring for another 1 hour at room temperature, the precipitates are filtered and washed with ethanol to yield a crude product of (−)-D-tartaric acid salt of amine (Ia). Yield=5.90 g; M.p.=155°–166° C.

Recrystallization 3 times from a mixture of methanol and acetone (1:2) gives purified tartaric acid salt of amine (Ia). Yield=1.28 g (14.1%); M.p.=169°–171° C.

Elemental analysis (as $C_{14}H_{23}NO_6$)

Calculated (%) ; C: 55.79; H: 7.71; N: 4.65

Found (%) ; C: 55.63; H: 7.58; N: 4.68

The salt of amine (Ia) (45 g) is treated with a base (1N NaOH) in a solvent (Hexane) at 0° C. The reaction mixture is extracted with dichloromethane. The organic solution is dried and concentrated to give (Ia). Yield=17.5 g; B.p.=62° C. (at 15 mm Hg).

$[\alpha]_D$=+26.3° (5% HCl aq. (35%)—ethanol ; C=1.0; 20.0° C.)

$^1$H NMR (CDCl$_3$) δppm: 0.78–0.93 (m, 1H), 1.15–1.80 (m, 8H), 1.91–1.96 (m, 1H), 2.00–2.14 (m, 3H), 2.73–2.79 (m, 1H), 4.95–5.10 (m, 2H), 5.81 (ddt, J=17, 10, 7Hz, 1H)

EXAMPLE 2

Preparation of Phenyl Sulfonamide Derivative

To a suspension of 600 mg (1.99 mM) of salt prepared in Example 1 in 20 ml of ethyl acetate are added 6.6 ml (1.99 mM×3.3) of 1N KOH and 2.79 μl (1.99 mM×1.1) of phenylsulfonyl chloride at 0° C. and the mixture is stirred for another 15 minutes at the same temperature. The reaction mixture is washed with 2N HCl, dried over sodium sulfate, and concentrated under reduced pressure. The residue is purified by silica gel column chromatography using 20 g of SiO$_2$ with a mixture of n-hexane and ethyl acetate (9:1) as eluent to obtain optically active sulfonamide (IIa). Yield= 300 mg (51.7%); M.p.=85°–94° C.

$[\alpha]_D$=+17.3°±0.6° (CHCl$_3$, C=1.000, 23° C.) 71.2%ee (pure standard=+24.3°±0.6°)

EXAMPLE 3

Optical Resolution of Racemic Mixture of Norbornyl Amine using N-acetyl-L-phenylalanine To a saturated solution of 2.07 g (10 mM) of N-acetyl-L-phenylalanine in ethanol at room temperature is added 3.02 g (20 mM) of racemic mixture of amine (Ia) and the mixture is allowed to stand for 30 minutes. The resultant precipitate of N-acetyl-L-phenylalanine salt of amine (Ia) is collected and recrystallized from ethanol (×2) to obtain the desired chiral salt. Yield=1.05 g (14.6%).

The resultant salt is then treated with base and phenylsulfonyl chloride in the same manner as described in Example 2 to obtain an optically active sulfonamide (IIa) (70.9%ee).

EXAMPLE 4

Optical Resolution of Racemic Mixture of Norbornyl Amine using N-acetyl-L-leucine To a solution of 1.54 g (8.89 mM) of N-acetyl-L-leucine in 10 ml of methanol is added 2.70 g (17.8 mM) of racemic mixture of amine (Ia) at 30° C. After the removal of methanol under reduced pressure, the residue is recrystallized from ethanol-ethyl acetate (5:6) (×2) to obtain N-acetyl-L-leucine salt of amine (Ia). Yield=0.55 g (9.5%).

The resultant chiral salt is then sulfonylated in the same manner as described in Example 2 to obtain an optically active sulfonamide (IIa) (77.7%ee).

EXAMPLE 5

Optical Resolution of Racemic Mixture of Norbornyl Amine using N-Boc-L-methionine To a solution of 2.49 g (10 mM) of N-Boc-L-methionine in 10 ml of ethanol is added 3.02 g (20 mM) of racemic mixture of amine (Ia) at room temperature and the mixture is allowed to stand for 1 hour. The resultant precipitate is collected by filtration and dried to obtain 2.26 g of crude N-Boc-L-methionine salt of amine (Ia). Recrystallization from ethanol-ethyl acetate (1:1) gives pure salt. Yield=1.27 g (15.9%).

The resultant chiral salt is then sulfonylated in the same manner as described in Example 2 to obtain an optically active sulfonamide (IIa). Yield=96.0%ee.

EXAMPLE 6

Optical Resolution of Racemic Mixture of Norbornyl Amine using N-acetyl-L-glutamic Acid To a solution of 3.0 g (16 mM) of N-acetyl-L-glutamic acid in 120 ml of methanol is added 3.02 g (20 mM) of racemic mixture of amine (Ia) at 30° C. The reaction mixture is concentrated under reduced pressure to remove methanol. Ethyl acetate is added to the residue and the resulting crystalline precipitates are collected by filtration. Recrystallization from ethanol-ethyl acetate (5:7) gives N-acetyl-glutamic acid salt of amine (Ia). Yield=1.40 g (20.6%).

The resultant chiral salt is then sulfonylated in the same manner as described in Example 2 to obtain an optically active sulfonamide (IIa) (91.7%ee).

The racemic mixture of amine (Ia) was resolved using various optically active acids and the resultant salts were converted into sulfonamides of formula (IIa) in the same manner as described in Examples 1 and 2. The results are summarized in the following Table 1.

TABLE 1

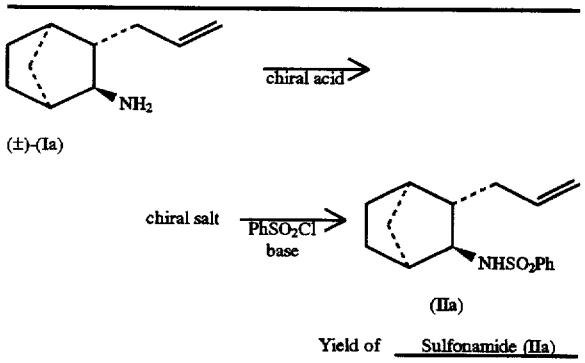

| resolving agent | recrystallization solvent | chiral salt of (Ia) | Sulfonamide (IIa) optical rotation | yield (ee) |
|---|---|---|---|---|
| (−)-D-tartaric acid | MeOH:acetone (3:10) × 3 | 14.1% | +17.3° ±0.6° | 71.2% |
| (−)-O-diacetyl-L-tartaric acid | EtOH | 12.9% | +12.9° | 53.1% |
| (−)-O-dibenzoyl-L-tartaric acid | EtOH | 10.7% | +7.3° | 30.0% |
| (−)-D-mandelic acid | acetone | 21.4% | +8.6° | 35.4% |
| N-acetyl-L-leucine | EtOH:AcOEt (5:6) × 2 | 9.5% | +18.9° | 77.7% |
| N-acetyl-L-phenyl alanine | EtOH | 14.6% | +12.2° | 70.9% |
| N-Boc-L-methionine | EtOH:AcOEt (1:1) | 15.9% | more than +22.2° | 96.0% |
| N-acetyl-L-glutamic acid | EtOH:AcOEt (5:7) | 20.6% | +22.3° | 91.7% |

*: The yield of salt is based on the starting material, amine (Ia) as a racemic mixture.

EXAMPLE 7

Preparation of Sulfonamide (IIa)

A mixture of 70.5 g (0.18 mole) of salt prepared in a similar manner as described in Examples 1, 3 to 6 and 335 g (1.1 mole) of 2.4% sodium hydroxide solution is stirred for 10 minutes at room temperature. The mixture is then extracted with 330 g of dichloromethane and the extract washed with 110 g of water. To the dichloromethane layer is added 21.4 g (1.2 mole) of triethylamine and the mixture stirred for 5 minutes, which is followed by the addition of 34.2 g (1.1 mole) of benzenesulfonyl chloride at 10°±5° C. The reaction mixture is reacted for 30 minutes at the same temperature and 224 g of ethanol is added thereto. After the mixture is condensed to about 280 ml under a reduced pressure, 329 ml of water is added dropwise to the residue over about 1 hour and the mixture stirred for 30 min at 20°±5° C. The precipitated crystalls are separated and air-dried to yield 50.3 g (yield 98%) of sulfonamide (IIa).

EXAMPLE 8

Preparation of Aldehyde (IIa')

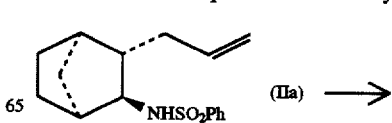

-continued

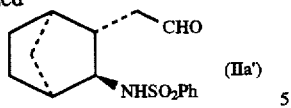
(IIa')

A solution of 33 g (0.11 mole) of sulfonamide (II) prepared in a similar manner as described in Examples 2 and 7 in 47.4 g of methanol and 798 g of dichloromethane is cooled at −65° C. and 5.4 g of ozone is introduced thereto until the solution turns into violet. After the removal of excessive ozone with nitrogen gas, a solution of 35.6 g (1.2 mole) of triphenylphosphine in 59 g of dichloromethane is added dropwise to the colored solution at −60°±5° C. over about 1 hour. The mixture is allowed to warm to 0°±3° C. and reacted at the same temperature for 3 hours. The reaction mixture is washed three times with 200 ml of water and evaporated to dryness under a reduced pressure to obtain a residue. The resultant crude aldehyde (IIa') is dissolved in 145 g of DMSO to give about 220 g of a solution which is used in the next step.

EXAMPLE 9

Preparation of (+)-S-145

A suspension of 65.3 g (1.3 mole) of 4-carboxybutyltriphenylphosphonium bromide in 110 g of DMSO and 87 g of toluene is cooled at 0°±+3° C. To the suspension is added 47 g (3.7 mole) of potassium t-butoxide and reacted for 1 hour. To the reaction mixture is added dropwise about 220 g of aldehyde (II') in DMSO (prepared in Example 8) at 0° to 5° C. After 1-hour-reaction at the same temperature, the reaction mixture is extracted with a mixture of 200 g of water and 200 g of toluene. The aqueous layer is taken, acidified to pH 1 with 69 g of 18% hydrochloride, and extracted with 378 g of ethyl acetate. The ethyl acetate layer is taken, washed twice with 160 g of 20% brine and condensed under a reduced pressure to about 60 ml containing the titled (+)-S-145, which is then dissolved in a mixture of 530 g of ethyl acetate and 904 g of dichloromethane. To the resultant solution is added a solution of 22.3 g (1.3 mole) of 4-methoxyphenethylamine in 80 g of ethyl acetate and reacted at 0° to 25° C. for 3 hours with stirring. After the reaction completes, the mixture is centrifuged to separate crystalline precipitates, which was washed with 180 g of ethyl acetate to give about 94 g of crude (+)-S-145 MPA salt as a wet crystal.

What we claim is:

1. A process for preparing a compound of formula (IV):

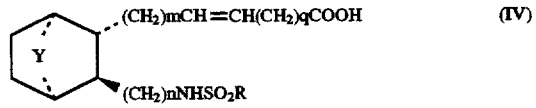
(IV)

wherein R is phenyl or phenyl substituted with hydroxy, lower alkoxy, halogen, or lower alkyl; Y is oxygen, methylene, substituted methylene; m is 0 or 1; n is 0, 1 or 2; q is 3 or 4 with the proviso that when m is 1, n is 0 or 1, which comprises the following reaction steps:

(a) resolving a compound of formula (I):

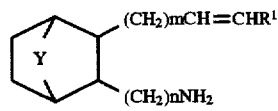
(I)

wherein $R^1$ is hydrogen, lower alkyl or lower alkyl substituted with —$COOR^3$ at the terminal methylene residue; $R^3$ is lower alkyl and Y, m and n are as defined above with a chiral acid selected from the group consisting of glutamic acid, N-acetyl-L- and N-tert-butoxycarbonyl-L-methionine in an alcoholic solvent to form a chiral salt;

(b) recovering an optically active amine of formula (I'):

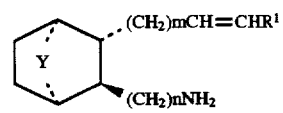
(I')

wherein $R^1$, Y, m and n are as defined above by treating the chiral salt obtained in step (a) with a base;

(c) reacting the optically active compound of formula (I') obtained in step (b) with a substituted sulfonyl halide of formula (III):

$RSO_2X$ (III)

wherein R is as defined above and X is halogen to yield an optically active sulfonamide derivative of formula (II):

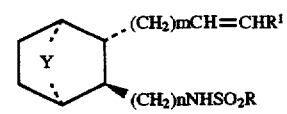
(II)

wherein $R^1$, R, Y, m, and n are as defined above;

(d) oxidizing the compound (II) prepared in step (c) to yield an aldehyde of formula (II'):

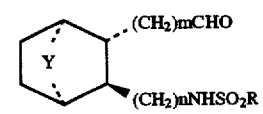
(II')

wherein R, Y, m, and n are as defined above; and (e) converting the aldehyde (II') prepared in step (d) into a compound of formula (IV) by a conventional method.

2. The process of claim 1 in which a chiral salt formed in the resolution of compound (I) is separated by filtration and treated with a base to obtain an optically active norbornyl amine of formula (I').

3. A process for preparing an optically active amine of formula (I')

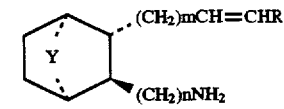
(I')

wherein $R^1$ is hydrogen, lower alkyl or lower alkyl substituted with $COOR^3$ at the terminal methylene residue; $R^3$ is lower alkyl, Y is oxygen, methylene or substituted methylene, m is 0 or 1, n is 0, 1 or 2 with the proviso that when m is 1, n is 0 or 1 which comprises (a) resolving a compound of formula (I)

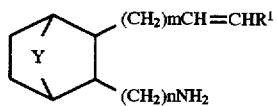

wherein $R^1$, Y, m and n are as defined above with a chiral acid selected from the group consisting of N-acetyl-L-glutamic acid and N-tert-butoxycarbonyl-L-methionine in an alcoholic solvent to form a chiral salt, and (b) recovering the optically active amine of formula (I') by treating the chiral salt obtained in step (a) with a base.

4. A process according to claim 1 in which the alcoholic solvent is selected from the group consisting of methanol, ethanol and propanol.

* * * * *